(12) United States Patent
Patel et al.

(10) Patent No.: US 9,382,178 B2
(45) Date of Patent: Jul. 5, 2016

(54) PROCESS FOR PRODUCING PHENOL

(71) Applicant: ExxonMobil Chemical Patents Inc., Baytown, TX (US)

(72) Inventors: Bryan A. Patel, Jersey City, NJ (US); John S. Coleman, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/787,862

(22) PCT Filed: Apr. 9, 2014

(86) PCT No.: PCT/US2014/033475
§ 371 (c)(1),
(2) Date: Oct. 29, 2015

(87) PCT Pub. No.: WO2014/189623
PCT Pub. Date: Nov. 27, 2014

(65) Prior Publication Data
US 2016/0075623 A1    Mar. 17, 2016

Related U.S. Application Data

(60) Provisional application No. 61/826,341, filed on May 22, 2013.

(30) Foreign Application Priority Data

Jul. 29, 2013  (EP) ..................................... 13178304

(51) Int. Cl.
| C07C 45/53 | (2006.01) |
| C07C 37/08 | (2006.01) |
| C07C 2/66 | (2006.01) |
| C07C 37/50 | (2006.01) |
| C07C 2/74 | (2006.01) |
| C07C 407/00 | (2006.01) |
| C07C 409/14 | (2006.01) |

(52) U.S. Cl.
CPC . *C07C 37/50* (2013.01); *C07C 2/74* (2013.01); *C07C 37/08* (2013.01); *C07C 45/53* (2013.01); *C07C 407/00* (2013.01); *C07C 409/14* (2013.01); *C07C 2101/14* (2013.01); *C07C 2529/70* (2013.01)

(58) Field of Classification Search
CPC .......... C07C 45/53; C07C 37/08; C07C 2/66; C07C 2/67
USPC ................................... 568/342, 798; 585/467
See application file for complete search history.

(56) References Cited

U.S. PATENT DOCUMENTS

| 6,037,513 A | 3/2000 | Chang et al. |
| 8,884,068 B2 | 11/2014 | Kuechler et al. |
| 2015/0251986 A1 | 9/2015 | Kuechler et al. |

FOREIGN PATENT DOCUMENTS

| GB | 681613 | 10/1952 |
| WO | 2010/042261 | 4/2010 |
| WO | 2012/036827 | 3/2012 |
| WO | 2012/067711 | 5/2012 |
| WO | 2012/118542 | 9/2012 |
| WO | 2012/145028 | 10/2012 |
| WO | 2013/043272 | 3/2013 |

*Primary Examiner* — Sikarl Witherspoon
(74) *Attorney, Agent, or Firm* — Siwen Chen; Stephen A. Baehl

(57) ABSTRACT

In a process for producing phenol and cyclohexanone, reaction components comprising cyclohexylbenzene hydroperoxide and an acid catalyst are supplied to a cleavage reaction zone, mixed under mixing conditions effective to combine the reaction components into a reaction mixture and at least part of the cyclohexylbenzene hydroperoxide in the reaction mixture is converted under cleavage conditions to into phenol and cyclohexanone; and a cleavage effluent is recovered from the cleavage reaction zone. The cleavage and mixing conditions are controlled such that the ratio $t_R/t_M$ is at least 10, where $t_R$ is the half-life of cyclohexylbenzene hydroperoxide under the cleavage conditions and $t_M$ is the time required after injection of a tracer material into the reaction mixture under the mixing conditions for at least 95% by volume of the entire reaction mixture to attain at least 95% of the volume-averaged tracer material concentration.

14 Claims, 4 Drawing Sheets

PROCESS FOR PRODUCING PHENOL

PRIORITY CLAIM

This application is a National Stage Application of International Application No. PCT/US2014/033475 filed Apr. 9, 2014, which claims priority to U.S. Provisional Application Ser. No. 61/826,341 filed May 22, 2013, and European Application No. 13178304.5 filed Jul. 29, 2013, the disclosures of which are fully incorporated herein by their reference.

FIELD

The present invention relates to a process for producing phenol.

BACKGROUND

Phenol is an important product in the chemical industry and is useful in, for example, the production of phenolic resins, bisphenol A, ε-caprolactam, adipic acid, and plasticizers.

Currently, a common route for the production of phenol is the Hock process via cumene. This is a three-step process in which the first step involves alkylation of benzene with propylene in the presence of an acidic catalyst to produce cumene. The second step is oxidation, preferably aerobic oxidation, of cumene to the corresponding cumene hydroperoxide. The third step is the cleavage of cumene hydroperoxide in the presence of heterogeneous or homogeneous catalysts into equimolar amounts of phenol and acetone. However, the world demand for phenol is growing more rapidly than that for acetone.

Thus, a process that coproduces a ketone other than acetone may be an attractive alternative route to the production of phenol. For example, there is a growing market for cyclohexanone, which is used as an industrial solvent, as an activator in oxidation reactions and in the production of adipic acid, cyclohexanone resins, cyclohexanone oxime, caprolactam and nylon 6.

Phenol and cyclohexanone can be co-produced by a variation of the Hock process in which cyclohexylbenzene is oxidized to obtain cyclohexylbenzene hydroperoxide and the hydroperoxide is decomposed in the presence of an acid catalyst to the desired phenol and cyclohexanone. Although various methods are available for the production of cyclohexylbenzene, a preferred route is disclosed in U.S. Pat. No. 6,037,513, which discloses that cyclohexylbenzene can be produced by contacting benzene with hydrogen in the presence of a bifunctional catalyst comprising a molecular sieve of the MCM-22 family and at least one hydrogenation metal selected from palladium, ruthenium, nickel, cobalt and mixtures thereof. This reference also discloses that the resultant cyclohexylbenzene can be oxidized to the corresponding hydroperoxide which is then decomposed to the desired phenol and cyclohexanone co-product.

Although the production of phenol and cyclohexanone from cyclohexylbenzene appears to be analogous to the Hock process for producing phenol and acetone from cumene, the chemistries in each step are actually very different. For example, the chemistry of the cleavage of cyclohexylbenzene hydroperoxide is much more complicated than that for cumene hydroperoxide and more by-products (both in types and amounts) can form. Thus, cleavage of cyclohexylbenzene hydroperoxide to phenol and cyclohexanone is acid catalyzed and, although a variety of acid catalysts can be used, sulfuric acid is preferred for its low cost and easy availability. However, significant yield loss to by-products (both primary and secondary) can occur in the sulfuric acid-based cleavage of cyclohexylbenzene hydroperoxide. Typical primary by-products include the β-scission products such as hexanophenone and 6-hydroxylhexanophenone (6-HHP). Examples of secondary by-products include those derived from cyclohexanone, such as 2-(1-cyclohexenyl)cylohexanone and 2-(cyclohexylidene)cyclohexanone (cyclohexanone aldol condensation products), 2-hydroxycyclohexanone and cyclohexenone (cyclohexanone oxidation products). Formation of the primary by-products results in loss of both phenol and cyclohexanone; while secondary by-products further reduce yield to cyclohexanone.

There is therefore significant interest in developing an acid-catalyzed process for the cleavage of cyclohexylbenzene hydroperoxide in which the yield of phenol and cyclohexanone is maximized. According to the invention, it has now been found that achieving high yields of phenol and cyclohexanone in the conversion of cyclohexylbenzene hydroperoxide in the presence of an acid catalyst is dependent not only on the composition of the cleavage reaction medium but also on the ratio of mixing rate to the reaction rate of the reaction components. In particular, it has been found that improved reaction selectivity is achieved when the ratio of $t_R/t_M \geq 10$, where $t_R$ is the half-life of cyclohexylbenzene hydroperoxide under the cleavage conditions employed and $t_M$ is a characteristic mixing time for the reaction components under the mixing conditions employed. The time $t_M$ is determined in a separate calibration test by injecting a tracer material into the reaction components and measuring the time under the mixing conditions employed in the cleavage process for at least 95% by volume of the entire reaction medium to reach at least 95% of the volume-averaged tracer material concentration.

SUMMARY

In one aspect, the present invention relates to a process for producing phenol and cyclohexanone, the process comprising:

(a1) supplying reaction components comprising cyclohexylbenzene hydroperoxide and an acid catalyst to a cleavage reaction zone;

(a2) mixing the reaction components under mixing conditions effective to combine the reaction components into a reaction mixture;

(a3) converting at least part of the cyclohexylbenzene hydroperoxide in the reaction mixture under cleavage conditions into phenol and cyclohexanone; and (b) recovering a cleavage effluent from the cleavage reaction zone, wherein the mixing (a2) is arranged such that the ratio $t_R/t_M$ is at least 10, where $t_R$ is the half-life of cyclohexylbenzene hydroperoxide under the cleavage conditions, and $t_M$ is the time required after injection of a tracer material into the reaction mixture under the mixing conditions for at least 95% by volume of the entire reaction mixture to attain at least 95% of the volume-averaged tracer concentration.

In one embodiment, the mixing (a2) comprises passing the reaction components through at least one of an in-line static mixer, an in-line orifice plate, an in-line swirl vane assembly and a pump.

In a further embodiment, the mixing (a2) comprises stirring the reaction components with one or more mechanical agitation devices.

In yet a further embodiment, the reaction components comprise at least a first stream and a second stream and the mixing (a2) comprises injecting the first stream into the second stream.

In one embodiment, the process further comprises:

(c) recycling part of the cleavage effluent to the cleavage reaction zone as a source of one or more of the reaction components.

In one embodiment, the process further comprises:

(d) hydroalkylating benzene with hydrogen in the presence of a first catalyst under conditions effective to produce a hydroalkylation product comprising cyclohexylbenzene;

(e) contacting at least part of the cyclohexylbenzene from (d) with oxygen in the presence of a second catalyst under oxidation conditions effective to produce an oxidation product comprising cyclohexylbenzene hydroperoxide;

(f) supplying at least part of the cyclohexylbenzene hydroperoxide from (e) to the cleavage reaction zone in (a1).

DETAILED DESCRIPTION OF THE EMBODIMENTS

Figure 1:
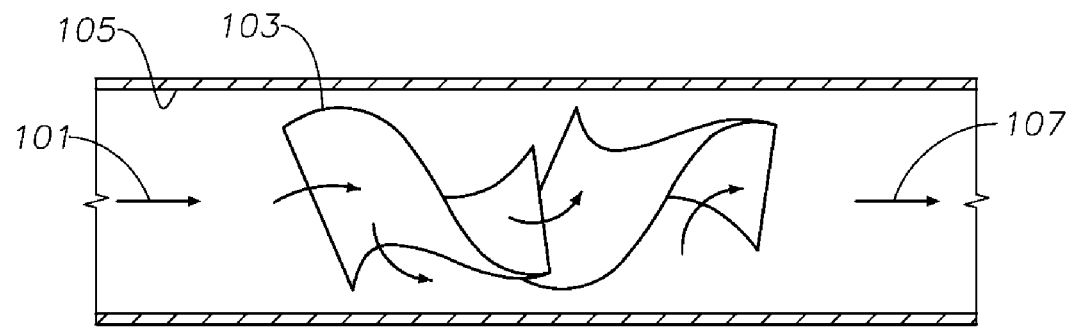
FIG. 1 is a schematic illustration of an in-line static mixer for use in mixing reaction components in accordance with a first example of the process of the invention.

In the present disclosure, a process may be described as comprising at least one "step." It should be understood that each step is an action or operation that may be carried out once or multiple times in the process, in a continuous or discontinuous fashion. Unless specified to the contrary or the context clearly indicates otherwise, each step in a process may be conducted sequentially in the order as they are listed, with or without overlapping with one or more other step, or in any other order, as the case may be. In addition, some steps may be conducted simultaneously, for example, in the same reaction zone.

Unless otherwise indicated, all numbers in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "an acid" include embodiments where one, two or more acids are used, unless specified to the contrary or the context clearly indicates that only one acid is used.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question unless specified or indicated otherwise. All ranges expressed herein should include both end points as two specific embodiments unless specified or indicated to the contrary.

As used herein, the term "cyclohexylbenzene" shall mean benzene substituted by a single cyclohexyl group, unless specified to the contrary or the context clearly indicates otherwise. As used herein, the generic term "dicyclohexylbenzene" shall include 1,2-dicyclohexylbenzene, 1,3-dicyclohexylbenzne, 1,4-dicyclohexylbenzene, and mixtures and combinations of at least two thereof in any proportion. As used herein, the generic term "tricyclohexylbenzene" shall include 1,2,3-tricyclohexylbenzene, 1,2,4-tricyclohexylbenzene and 1,3,5-tricyclohexylbenzene, and combinations and mixtures thereof at any proportion. The generic term "polycyclohexylbenzene" shall include any of the dicyclohexylbenzene isomers and tricyclohexylbenzene isomers described above, and combinations and mixtures of at least two thereof in any proportion.

Described herein is a process for producing phenol and cyclohexanone by cleavage of cyclohexylbenzene hydroperoxide in the presence of an acid catalyst, e.g., an acid in the liquid phase such as sulfuric acid. In the process, the reaction components comprising cyclohexylbenzene hydroperoxide and the liquid-phase acid catalyst are supplied to a cleavage reaction zone, mixed under mixing conditions effective to combine the reaction components into a reaction mixture and, and at least part of the cyclohexylbenzene hydroperoxide in the reaction mixture is then converted under cleavage conditions into phenol and cyclohexanone. In particular, the cleavage and mixing conditions are controlled such that $t_R/t_M$ is at least R1, where R1 can be 10, 20, 30, 40, 50, 60, 70, 80, 90, 100, 110, 120, 130, 140, 150, 180, or even 200. In embodiments, the ratio $t_R/t_M$ is at most R2, where R2 can be 500, 450, 400, 350, 300, 250, 200, 180, 160, 150, 140, 120, 100, 80, 60, 50, 40, 30, as long as R2≥R1. As used herein, $t_R$ is the half-life of cyclohexylbenzene hydroperoxide under the cleavage conditions employed, and $t_M$ is a characteristic mixing time for the reaction components under the mixing conditions employed. The determination of the parameters $t_R$ and $t_M$ will be described in more detail below.

Although the reasons for the importance of the $t_R/t_M$ ratio are not fully understood, it is believed that, since the acid catalyzed cleavage of cyclohexylbenzene hydroperoxide is a rapid and highly exothermic reaction, effective mixing of all liquid phase species is highly desirable to ensure optimal reaction performance. It is also believed that locally high catalyst or reactant concentrations can lead to unfavorable side reactions that reduce overall reaction selectivity so that selecting the parameters $t_R$ and $t_M$ such that $t_R/t_M$ is at least 10 enhances selectivity.

In one embodiment, the present cleavage process forms part of an integrated process for producing phenol from benzene in which the benzene is initially alkylated or hydroalkylated to produce cyclohexylbenzene and the cyclohexylbenzene is oxidized to produce cyclohexylbenzene hydroperoxide. The ensuing description will therefore focus on this integrated process. It should be understood, however, that the cyclohexylbenzene hydroperoxide used in the process of the present disclosure may be made by other means.

Production of Cyclohexylbenzene

The cyclohexylbenzene starting material for the present process can be produced by the alkylation of benzene with cyclohexene according to the following reaction:

The cyclohexene can be supplied to the reaction zone as a separate feed from the benzene, or produced in situ by the selective hydrogenation of benzene in the presence of a bifunctional catalyst. Such a reaction is generally termed "hydroalkylation" and may be summarized as follows:

Any commercially available benzene feed can be used in the hydroalkylation step, but in one embodiment the benzene has a purity level of at least 99 wt %. Similarly, although the source of hydrogen is not critical, it is desirable that the hydrogen is at least 99 wt % pure.

In certain embodiments, the total feed to the hydroalkylation step contains, by weight of the total weight of the feed, at most Cw ppm of water, where Cw can be 1000, 900, 800, 700, 600, 500, 400, 300, 200, 100, or even 50. In addition, the total feed may contain, by weight of the total weight of the feed, at most Cs ppm of sulfur and at most Cn ppm of nitrogen, where Cs can be 100, 90, 80, 70, 60, 50, 40, 30, 20, 10, 8, 6, 5, 4, 3, 2, or even 1; and Cn can be 10, 8, 6, 5, 4, 3, 2, 1, 0.8, 0.6, 0.5, 0.3, 0.2, or even 0.1.

Hydrogen can be supplied to the hydroalkylation step over a wide range of values, but the hydrogen supply is desirably arranged such that the molar ratio of hydrogen to benzene in the hydroalkylation feed is from about 0.15:1 to about 15:1, such as from about 0.4:1 to about 4:1, for example from about 0.4:1 to about 0.9:1, e.g., 0.5:1, 0.6:1, 0.7:1 or 0.8:1.

In addition to benzene and hydrogen, a diluent, which is substantially inert under hydroalkylation conditions, may be supplied to the hydroalkylation reaction. In certain embodiments, the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, advantageously the diluent is added in an amount such that the weight ratio of the diluent to the aromatic compound is at least 1:100; for example at least 1:10, but no more than 10:1, for example no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are from about 100° C. to about 400° C., such as from about 125° C. to about 250° C., while suitable reaction pressures are from about 100 kPa to about 7,000 kPa, such as from about 500 kPa to about 5,000 kPa.

The catalyst employed in the hydroalkylation reaction is a bifunctional catalyst comprising a hydrogenating metal component and an alkylating solid acid component. Advantageously, the alkylating solid acid component comprises a molecular sieve of the MCM-22 family. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), and mixtures and combinations thereof. Molecular sieves similar to MCM-22 family materials, such as UZM-8 (described in U.S. Pat. No. 6,756,030), may be used alone or together with the MCM-22 family materials. Desirably, the molecular sieve useful in the hydroalkylation process is selected from (a) MCM-49; (b) MCM-56; and (c) isotypes of MCM-49 and MCM-56, such as ITQ-2.

Any known hydrogenating metal can be employed in the hydroalkylation catalyst, although suitable metals include palladium, ruthenium, nickel, zinc, tin, and cobalt, with palladium being particularly advantageous. Desirably, the amount of hydrogenating metal present in the catalyst is from about 0.05 wt % to about 10 wt %, such as from about 0.1 wt % to about 5 wt %, of the catalyst. In one embodiment, where the MCM-22 family molecular sieve is an aluminosilicate, the amount of hydrogenating metal present is such that the molar ratio of the aluminum in the molecular sieve to the hydrogenating metal is from about 1.5 to about 1500, for example from about 75 to about 750, such as from about 100 to about 300.

The hydrogenating metal may be directly supported on the MCM-22 family molecular sieve by, for example, impregnation or ion exchange. However, in certain embodiments, at least 50 wt %, for example at least 75 wt %, and desirably substantially all of the hydrogenating metal is supported on an inorganic oxide separate from but composited with the molecular sieve. In particular, it is found that by supporting the hydrogenating metal on the inorganic oxide, the activity of the catalyst and its selectivity to cyclohexylbenzene and dicyclohexylbenzene are increased as compared with an equivalent catalyst in which the hydrogenating metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenating metal can be deposited on the inorganic oxide, in certain embodiments by impregnation, before the metal-containing inorganic oxide is composited with the molecular sieve. In certain embodiments, the catalyst composite is produced by co-pelletization, in which a mixture of the molecular sieve and the metal-containing inorganic oxide are formed into pellets at high pressure (desirably about 350 kPa to about 350,000 kPa), or by co-extrusion, in which a slurry of the molecular sieve and the metal-containing inorganic oxide, optionally together with a separate binder, are forced through a die. If necessary, additional hydrogenating metal can subsequently be deposited on the resultant catalyst composite.

Although the hydroalkylation reaction using an MCM-22 family zeolite catalyst is highly selective towards cyclohexylbenzene, the effluent from the hydroalkylation reaction will inevitably contain some dicyclohexylbenzene by-product. Depending on the amount of this dicyclohexylbenzene, it may be desirable to either (a) transalkylate the dicyclohexylbenzene with additional benzene or (b) dealkylate the dicyclohexylbenzene to maximize the production of the desired monoalkylated species.

Transalkylation with additional benzene may be conducted in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y and mordenite. The transalkylation reaction is desirably conducted under at least partial liquid phase conditions, which suitably include a temperature of about 100 to about 300° C., an absolute pressure of about 800 to about 3500 kPa, a weight hourly space velocity of about 1 to about 10 hr$^{-1}$ on total feed, and a benzene/dicyclohexylbenzene weight ratio about of 1:1 to about 5:1.

Dealkylation or cracking may also be effected in a reactor separate from the hydroalkylation reactor, such as a reactive distillation unit, at a temperature of about 150° C. to about 500° C. and an absolute pressure of 15 to 500 psig (200 to 3550 kPa) over an acid catalyst such as an aluminosilicate, an aluminophosphate, a silicoaluminophosphate, amorphous silica-alumina, an acidic clay, a mixed metal oxide, such as $WO_x/ZrO_2$, phosphoric acid, sulfated zirconia and mixtures thereof. Desirably, the acid catalyst includes at least one aluminosilicate, aluminophosphate or silicoaluminophosphate of the FAU, AEL, AFI and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is desirably from 0 to about 0.9, such as from about 0.01 to about 0.5. Similarly, although the dealkylation reaction can be conducted in the absence of added hydrogen, hydrogen is advantageously introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

Another significant by-product of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluents mentioned above.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least part of the cyclohexane in the $C_6$-rich stream portion to benzene, which again can be recycled to the hydroalkylation reaction. The dehydrogenation catalyst desirably comprises (a) a support; (b) a hydrogenation-dehydrogenation component and (c) an inorganic promoter. In certain embodiments, the support (a) is selected from the group consisting of silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium and compounds and mixtures thereof. Desirably, the hydrogenation-dehydrogenation component is present in an amount from about 0.1 wt % to about 10 wt % of the catalyst. A suitable inorganic promoter (c) comprises at least one metal or compound thereof selected from Group 1 or Group 14 of the Periodic Table of Elements, such as a potassium compound or a tin compound. The promoter may be present in an amount from about 0.1 wt % to about 5 wt % of the catalyst. Suitable dehydrogenation conditions include a temperature of about 250° C. to about 500° C., an absolute pressure of about atmospheric to about 500 psig (100 to 3550 kPa), a weight hourly space velocity of about 0.2 to 50 hr$^{-1}$, and a hydrogen to hydrocarbon feed molar ratio of about 0 to about 20.

Other disadvantageous impurities of the hydroalkylation reaction are bicyclohexyl (BCH) and the methylcyclopentylbenzene (MCPB) isomers which, because of the similarity in their boiling points, are difficult to separate from the desired cyclohexylbenzene by distillation. Moreover, although 1,2-methylcyclopentylbenzene (2-MCPB), and 1,3-methylcyclopentylbenzene (3-MCPB) are readily converted in the subsequent oxidation/cleavage steps to the phenol and methylcyclopentanones, which are valuable products, 1,1-methylcyclopentylbenzene (1-MCPB) is substantially inert to the oxidation step and so, if not removed, will build up in the $C_{12}$ stream. Similarly, bicyclohexyl (BCH) can lead to separation problems downstream. Thus, at least part of the hydroalkylation reaction product may be treated with a catalyst under conditions to remove at least 1,1-methylcyclopentylbenzene and/or bicyclohexyl from the product. The catalyst can be an acid catalyst in certain embodiments, such as an aluminosilicate zeolite, and especially faujasite and the treatment is conducted at a temperature of about 100° C. to about 350° C., such as about 130° C. to about 250° C., for a time of about 0.1 to about 3 hours, such as about 0.1 to about 1 hour. The catalytic treatment is believed to isomerize the 1,1-methylcyclopentylbenzene to the more readily oxidizable 1,2-methylcyclopentylbenzene (2-MCPB), and 1,3-methylcyclopentylbenzene (3-MCPB). The bicyclohexyl is believed to react with benzene present in the hydroalkylation reaction product to produce cyclohexane and more of the desired cyclohexylbenzene according to the following reaction:

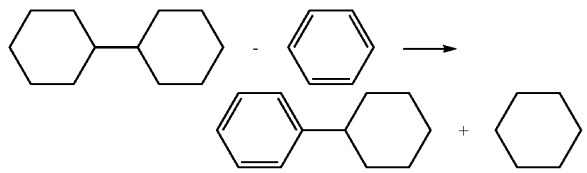

The catalytic treatment can be conducted on the direct product of the hydroalkylation reaction or after distillation of the hydroalkylation reaction product to separate the $C_6$ and/or the heavies fraction.

The cyclohexylbenzene product from the hydroalkylation reaction and any downstream reaction to remove the impurities discussed herein is separated from the reaction effluent(s) and is fed to the oxidation reaction described in more detail below.

Cyclohexylbenzene Oxidation

In order to convert the cyclohexylbenzene into phenol and cyclohexanone, the cyclohexylbenzene is initially oxidized to the corresponding hydroperoxide, particularly cyclohexyl-1-phenyl-1-hydroperoxide. This is accomplished by contacting the cyclohexylbenzene with an oxygen-containing gas, such as air and various derivatives of air. For example, it is possible to use air that has been compressed and filtered to removed particulates, air that has been compressed and cooled to condense and remove water, or air that has been enriched in oxygen above the natural approximately 21 mol % in air through membrane enrichment of air, cryogenic separation of air or other conventional means.

The oxidation step can be conducted autogeneously or more preferably in the presence of a catalyst. Although any catalyst can be employed, a preferred oxidation catalyst includes an N-hydroxy substituted cyclic imide described in U.S. Pat. No. 6,720,462, which is incorporated herein by reference in its entirety for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy (pyromellitic diimide), N,N'-dihydroxy(benzophenone-3,3', 4,4'-tetracarboxylic diimide), N-hydroxymaleimide, pyridine-2,3-dicarboximide, N-hydroxysuccinimide, N-hydroxy (tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxyphthalimide sodium salt or N-hydroxy-o-benzenedisulphonimide may be used. In one embodiment, the catalyst is N-hydroxyphthalimide. Another suitable catalyst is N,N',N"-trihydroxyisocyanuric acid. Each of the above cyclic imide catalysts contains the heteroatom nitrogen.

These oxidation catalysts can be used either alone or in conjunction with a free radical initiator, and further can be used as liquid-phase, homogeneous catalysts or can be supported on a solid carrier to provide a heterogeneous catalyst. Desirably, the N-hydroxy substituted cyclic imide or the N,N',N"-trihydroxyisocyanuric acid is employed in an amount from 0.0001 wt % to 15 wt %, such as from 0.001 wt % to 5 wt %, of the cyclohexylbenzene.

Suitable conditions for the oxidation step include a temperature from about 70° C. to about 200° C., such as about 90° C. to about 130° C., and an absolute pressure of about 50 to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaceously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Desirably, the product of the cyclohexylbenzene oxidation reaction contains at least 5 wt %, such as at least 10 wt %, for example at least 15 wt %, or at least 20 wt % cyclohexyl-1-phenyl-1-hydroperoxide based upon the total weight of the oxidation reaction effluent. In various embodiments, the oxidation reaction effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation reaction effluent.

The oxidation reaction effluent will also typically comprise residual cyclohexylbenzene. For example, the oxidation reaction effluent may include residual cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

Treatment of the Oxidation Reaction Effluent

In addition to cyclohexylbenzene hydroperoxide and unreacted cyclohexylbenzene, the oxidation reaction effluent may also contain some of the cyclic imide used as a catalyst in the oxidation reaction. Since cyclic imides are expensive and can act as poisons to downstream reactions, it is desirable to remove and/or recover at least part of the cyclic imide from the oxidation reaction effluent for recycle back to the oxidation step. In one embodiment, removal of the cyclic imide comprises contacting the oxidation reaction effluent with an aqueous solution of a base, particularly a weak base having a pKb value greater than or equal to the pKa of the cyclic imide of the first catalyst, whereby the imide is extracted into the aqueous phase, leaving an organic phase which comprises said oxidized hydrocarbon product and a reduced level of cyclic imide. In another embodiment, treatment of the oxidation effluent to remove at least part of the cyclic imide comprises contacting the effluent with an effective solid sorbent, such as a metal oxide or a metal carbonate and/or bicarbonate.

Prior to feeding to the cleavage step, the oxidation reaction effluent may be treated to increase the concentration of the cyclohexylbenzene hydroperoxide. Suitable concentration steps include fractional distillation to remove at least part of the higher boiling cyclohexylbenzene and fractional crystallization to separate solid cyclohexylbenzene hydroperoxide from the oxidation reaction effluent. In certain embodiments, the concentration step(s) are used to produce a cleavage feed containing greater than 40 wt % and no greater than 95 wt %, for example from 60 wt % to 85 wt %, of cyclohexylbenzene hydroperoxide, and at least 5 wt % and less than 60 wt %, for example from 15 wt % to 40 wt %, of cyclohexylbenzene.

Hydroperoxide Cleavage

The final reactive step in the present process for the conversion of the cyclohexylbenzene into phenol and cyclohexanone involves the acid, in certain embodiments liquid acid, -catalyzed cleavage of the cyclohexyl-1-phenyl-1-hydroperoxide produced in the oxidation step. The catalyst employed in the cleavage reaction is an acid which is at least partially soluble in the cleavage feed, is stable at a temperature of at least 185° C. and has a lower volatility (higher normal boiling point) than cyclohexylbenzene. Desirably, the acid catalyst is also at least partially soluble in the cleavage reaction product. Suitable acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide and sulfur trioxide. Desirably, the acid catalyst comprises sulfuric acid. In one embodiment, the concentration of sulfuric acid in the cleavage reaction mixture is from 50 to 5000 wpm by weight.

Cyclohexylbenzene hydroperoxide cleavage is a rapid liquid phase reaction occurring through the action of the acid catalyst and is often conducted in the presence of the cleavage products, mainly phenol and cyclohexanone. Water may be added, either separately or with the sulfuric acid, to tune the reaction chemistry. The appropriate mixing of these components—feed cyclohexylbenzene hydroperoxide, product phenol and cyclohexanone, sulfuric acid catalyst and, optionally, water—is highly desirable to achieving acceptable reaction selectivity. In particular, it has now been found that it is desirable to select the rate of mixing of the reaction components and the rate of cleavage of the cyclohexylbenzene hydroperoxide such that the ratio of $t_R/t_M$ is at least R1, where R1 can be 10, 20, 30, 40, 50, 60, 70, 80, 90, 100, 110, 120, 130, 140, 150, 180, or even 200. In embodiments, the ratio $t_R/t_M$ is at most R2, where R2 can be 500, 450, 400, 350, 300, 250, 200, 180, 160, 150, 140, 120, 100, 80, 60, 50, 40, 30, as long as R2≥R1. 10, such as at least 50, for example, at least 100, where $t_R$ and $t_M$ have the meaning described below.

The half-life $t_R$ of cyclohexylbenzene hydroperoxide is the time needed for half of the cyclohexylbenzene hydroperoxide to be depleted in the cleavage reaction and can be determined from the first order reaction rate constant, k, of the reaction according to the equation:

$$t_R = 0.6931/k.$$

The first order reaction rate constant, k, of the cleavage reaction depends on a number of parameters including but are not limited to the cyclohexylbenzene hydroperoxide concentration, A, the temperature, the acid concentration and the water concentration. For a given cleavage system, the value of k can be determined by plotting a graph of ln [A] against time. The slope of the straight line graph is equal to –k. In some embodiments, k ranges from 0.1 to 20 $min^{-1}$, which leads to values of $t_R$ from as low as 2.1 seconds to as high as 48 seconds.

The characteristic mixing time $t_M$ is determined in a separate calibration test. This test is conducted by injecting a pulse of tracer material at a point into the reaction components at the location of the mixing zone and measuring the time under the mixing conditions employed in the cleavage system for at least 95% (such as 95%, 96%, 97%, 98%, 99%, or even 99.5%) by volume of the entire reaction medium to reach at least 95% of the volume-averaged concentration of the tracer material, based on local measurements of tracer material concentration at various locations in the reaction medium. The tracer material is desirably soluble in the reaction medium, yet not reactive with the components of the reaction medium. For example, radioactively labeled biphenyl may be used as the tracer material in the process of the present invention. The concentration of the tracer material at a given location can therefore be conveniently measured by using a Geiger counter. The volume-averaged concentration of the tracer material is calculated by dividing the total amount of the tracer material injected by the entire volume of the reaction medium.

Various non-limiting examples of suitable devices for achieving the required mixing of the reaction components are shown in the accompanying drawings.

Thus, FIG. 1 shows an inline static mixer for mixing two or more liquid reaction components in a liquid feed stream 101. The mixer comprises a plurality of helical obstructions 103 mounted in a pipe 105. The feed stream 101 flows through the pipe 105 over the helical obstructions 103 which enhance mixing of the reaction components through increased rotational flow in the pipe 105. A mixed process stream 107 is produced with reduced radial gradients in concentration and temperature as compared with the feed stream 101.

Figure 2:
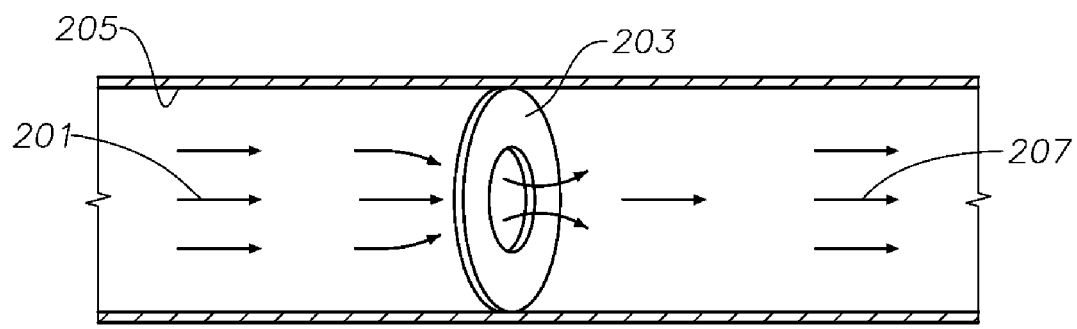
FIG. 2 is a schematic illustration of an in-line orifice plate for use in mixing reaction components in accordance with a second example of the process of the invention.

FIG. 2 shows an orifice plate 203 for mixing two or more liquid reaction components in a liquid feed stream 201 flowing through a pipe 205. The orifice plate 203 enhances mixing of the reaction components in the liquid feed stream 201 through increased shear and pressure drop in the pipe 205. The orifice plate 203 produces a sudden constriction in the pipe diameter which concentrates the liquid flow in the center of the pipe 205 and produces a mixed process stream 207 with increased homogeneity as compared with the feed stream 201.

Figure 3:
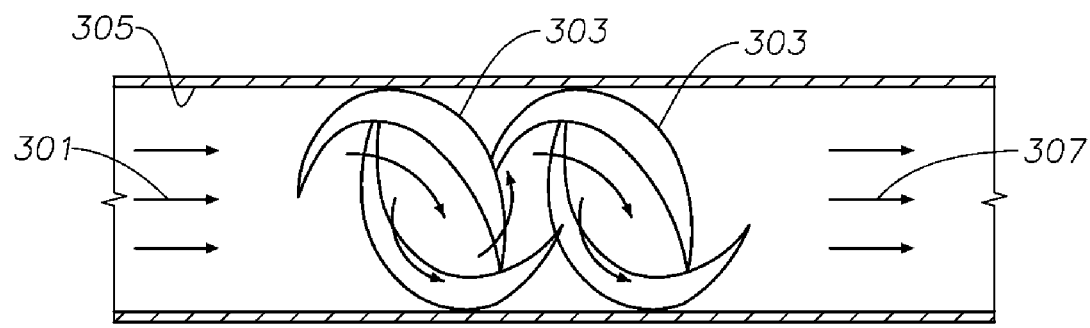
FIG. 3 is a schematic illustration of an in-line swirl vane assembly for use in mixing reaction components in accordance with a third example of the process of the invention.

FIG. 3 shows a mixer with swirl vanes 303 in a pipe 305 to enhance mixing of two or more liquid reaction components in a liquid feed stream 301 through increased rotational motion in the pipe 305. The swirl vanes 303 comprise crescent-shaped obstructions attached to the periphery of the pipe 305 and twisted down the length of pipe 305. Again, the rotational motion generated by the swirl vanes 303 produces a mixed process stream 307 with reduced radial gradients in concentration and temperature as compared with the feed stream 301.

Figure 4A:
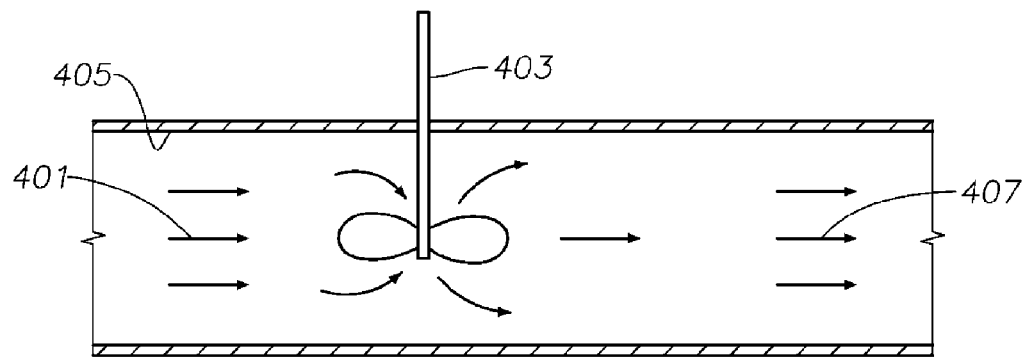
FIG. 4a and FIG. 4b are schematic illustrations of mechanical stirrers for use in mixing reaction components in accordance with a fourth example of the process of the invention.
Figure 4B:
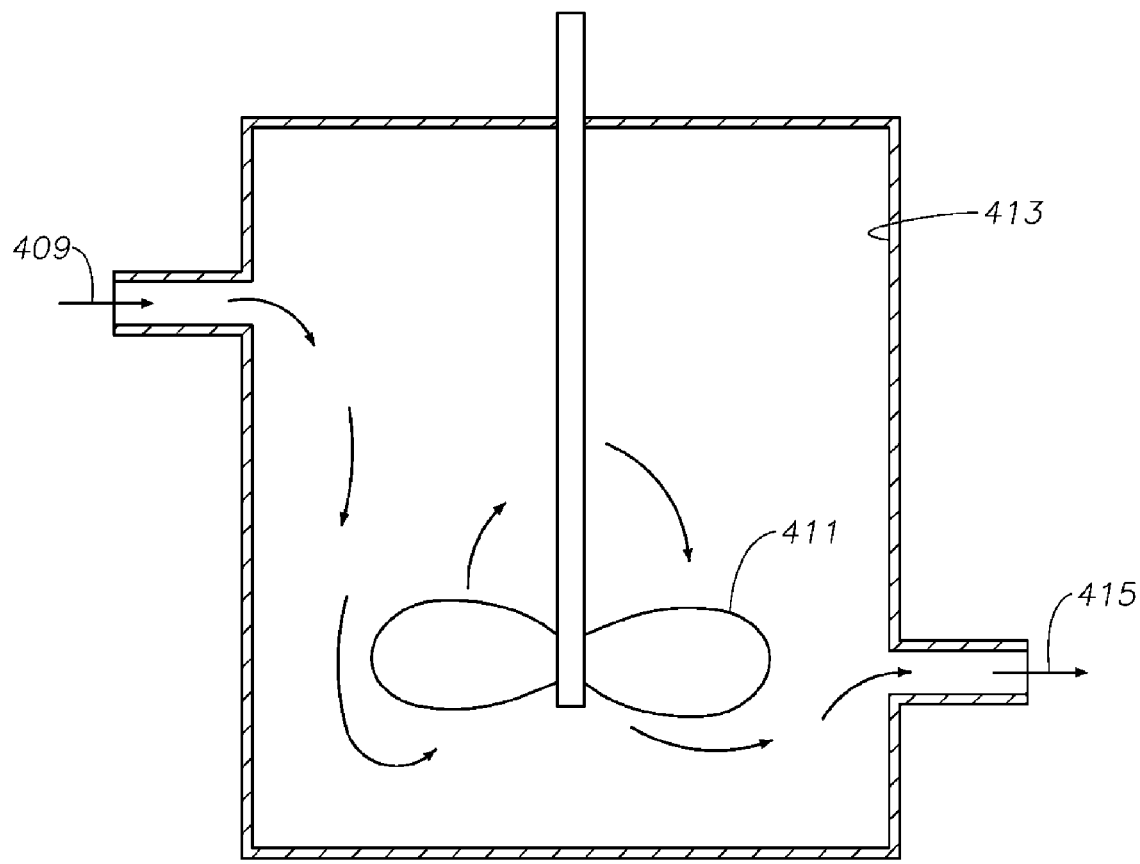

In FIG. 4a mixing of two or more liquid reaction components in a liquid feed stream 401 comprises mechanical agitation of the feed stream 401 using a rotating stirrer 403 mounted in a pipe 405 to produce a mixed process stream 407. A similar arrangement is shown in FIG. 4b, in which the feed stream 409 is mechanically agitated by a rotating stirrer 411 mounted in a tank 413 and a mixed process stream 415 is removed from the tank.

Figure 5:
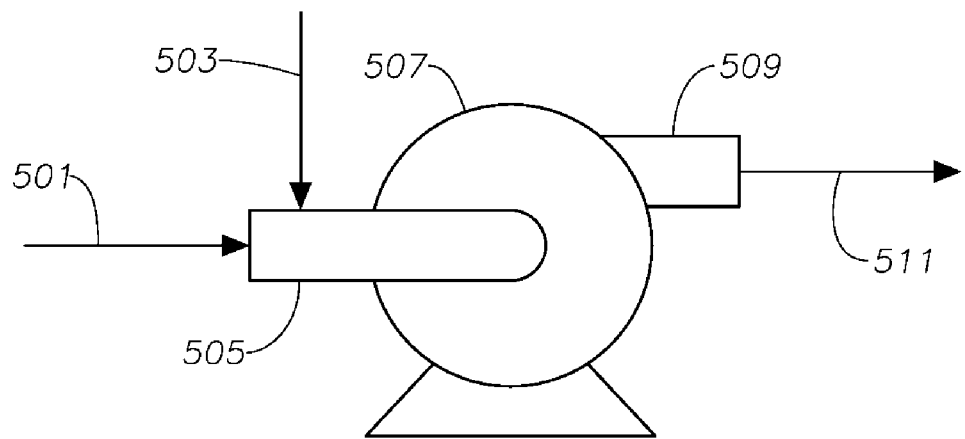
FIG. 5 is a schematic illustration of a pump for use in mixing reaction components in accordance with a fifth example of the process of the invention.

FIG. 5 shows an embodiment in which two liquid reaction component streams 501, 503 are supplied to the inlet side 505 of a pump 507 which mixes the reaction components to produce a mixed process stream 511 which is discharged from the outlet side 509 of the pump 507.

The embodiments shown in FIGS. 1 to 5 exemplify in-line methods to enhance mixing after two or more liquid reaction components are initially brought into contact. To enhance initial micro-mixing, a first stream containing at least one reaction component can be injected into a second stream containing at least a further reaction component using a device to increase shear and distribute the first stream more effectively into the second stream. Suitable injection devices are shown in FIG. 6a, FIG. 6b, and FIG. 7.

Figure 6A:
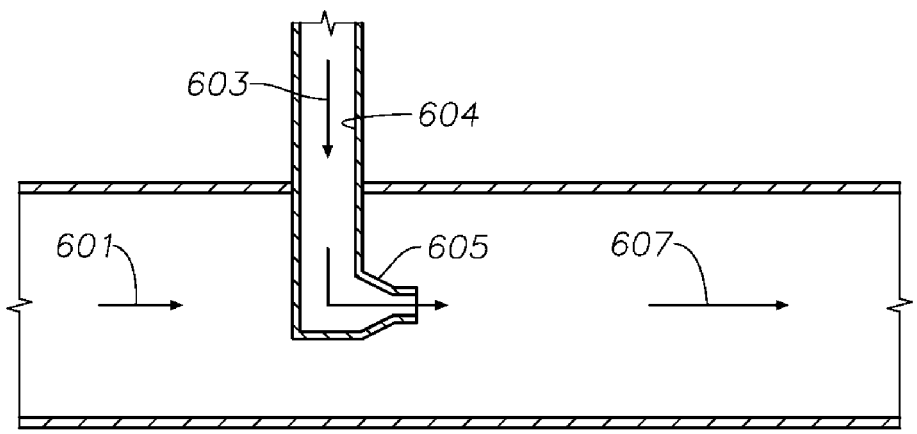
FIG. 6a and FIG. 6b are schematic illustrations of single outlet nozzles for use in mixing reaction components in accordance with a sixth example of the process of the invention.

In FIG. 6a, a first stream 603 is injected into a second stream 601 through an injection device 604 including a constricted nozzle 605. The constriction in the nozzle 605 increases the pressure drop in the first stream 603 and creates smaller droplets with increased velocity to produce a mixed process stream 607 with increased homogeneity. A similar arrangement is shown in FIG. 6b, although in the latter a first stream 611 is injected into a second stream 609 through a pipe 613 over a simple T-junction to produce a mixed process stream 615. The embodiments of FIG. 6a and FIG. 6b are especially desirable when the first stream has a much lower flow rate than the second stream, such as in the introduction of water or sulfuric acid catalyst to a combined stream containing feed cyclohexylbenzene hydroperoxide and product phenol and cyclohexanone.

Figure 6B:
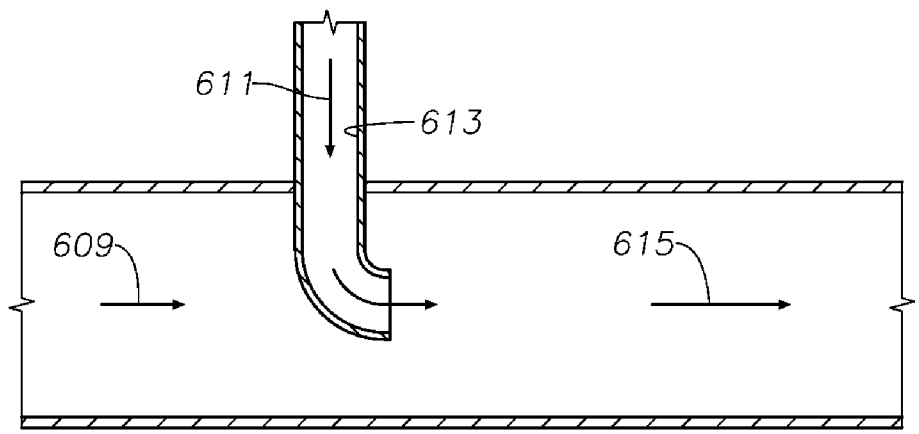
Figure 7:
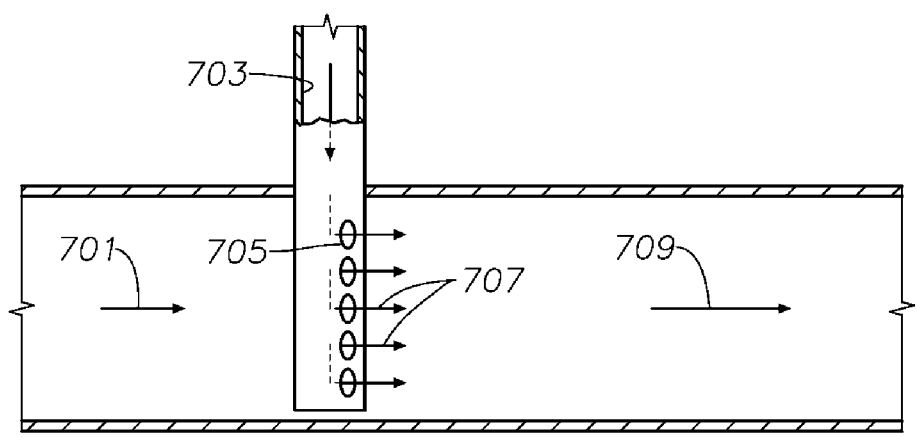
FIG. 7 is a schematic illustration of a multiple outlet nozzle for use in mixing reaction components in accordance with a seventh example of the process of the invention.

FIG. 6a and FIG. 6b show embodiments having single outlet nozzles to effect mixing. FIG. 7 illustrates an embodiment in which a first stream 703 is injected into a second stream 701 through an injection device 705 having multiple outlet nozzles 707. This arrangement distributes the liquid in the first stream 703 more effectively into the second stream 701 across the reaction zone cross-section and increases liquid-liquid interfacial area in the resulting mixed process stream 709. The embodiment of FIG. 7 is useful for higher flow rates in the first stream, which may occur in the introduction of fresh cyclohexylbenzene hydroperoxide into the second stream.

It is to be appreciated that more than one of the mixing methods disclosed in FIGS. 1 to 7 can be used in combination to produce a cleavage reaction mixture from any given set of reaction components.

In one embodiment, mixing of the cleavage reaction components is arranged to produce a cleavage reaction mixture containing from 1 wt % to 60 wt % cyclohexylbenzene hydroperoxide, from 1 wt % to 40 wt % cyclohexylbenzene, from 0.1 wt % to 4 wt % water, and from 10 wppm to 1000 wppm sulfuric acid. In some embodiment, the cleavage reaction mixture may also contain from 20 wt % to 70 wt % phenol and from 20 wt % to 50 wt % cyclohexanone.

Adjustment of the composition of the cleavage reaction mixture may be achieved by mixing the cleavage feed with a recycle stream comprising part of the cleavage effluent since the latter contains phenol, cyclohexanone, optionally cyclohexylbenzene hydroperoxide, cyclohexylbenzene, water and sulfuric acid. In some embodiments, mixing with the cleavage recycle stream may be sufficient to achieve the desired reaction mixture composition. Where necessary, however, the desired water content in the cleavage reaction mixture can be obtained by one or more of adding water to the cleavage feed, mixing the cleavage feed with the cleavage recycle stream and with water, adding water to the cleavage recycle stream, and adding water to the cleavage effluent. Similarly, the desired sulfuric acid content in the cleavage reaction mixture can be obtained by one or more of adding sulfuric acid to the cleavage feed, mixing the cleavage feed with the cleavage recycle stream and with sulfuric acid, adding sulfuric acid to the cleavage recycle stream, and adding sulfuric acid to the cleavage effluent followed by recycling a part thereof. In addition, the desired phenol content in the cleavage reaction mixture can be obtained by one or more of adding phenol to the cleavage feed, mixing the cleavage feed with the cleavage recycle stream and with phenol, adding phenol to the cleavage recycle stream, and adding phenol to the cleavage effluent followed by recycling a part thereof.

The cleavage reaction mixture may also contain a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less such as acetone, methylethyl ketone, 2- or 3-pentanone, cyclohexanone, and methylcyclopentanone. In one embodiment, the polar solvent is phenol and/or cyclohexanone recycled from the cleavage product after cooling. Advantageously, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 wt % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone and phenylcyclohexanol.

The cleavage reaction conditions are desirably selected so that the cleavage reaction mixture is completely or predominantly in the liquid phase during the cleavage reaction. In one embodiment, the cleavage reaction is conducted for a time sufficient to convert at least 50%, desirably at least 75%, of the cyclohexyl-1-phenyl-1-hydroperoxide in the cleavage reaction mixture and produce a cleavage effluent containing phenol and cyclohexanone.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. In one embodiment, cooling coils operating within the cleavage reactor(s) remove at least part of the heat generated.

The major products of the cleavage reaction are phenol and cyclohexanone, which are present in substantially equimolar amounts and, by virtue of the present process, are obtained in high yield. On leaving the cleavage reactor, the cleavage effluent may be cooled and thereafter separated into a product stream, from which the phenol and cyclohexanone products can be recovered, and a cleavage recycle stream, which can be mixed with the cleavage feed. Separation of the cleavage recycle stream can be effected without prior modification of the composition of cleavage effluent so that the recycle stream is composed of an aliquot of the cleavage effluent. In one embodiment, the cleavage recycle has substantially the same composition as the cleavage effluent, e.g., the variation of compositions between the cleavage recycle and the cleavage effluent is within 2 wt %, or even within 1 wt %, with respect to any given species content, for example, as may be indirectly affected by reactions occurring in the cleavage recycle in conveyance to the mixing with the cleavage feed. Thus, the cleavage feed may further be mixed with cyclohexylbenzene, in addition to at least phenol, cyclohexanone, water and sulfuric acid, for example, as may all be present in the portion of the cleavage effluent allocated as cleavage recycle.

Alternatively, the cleavage effluent or a portion thereof can be treated, for example, by fractionation, to separate the by-products and/or other components of the cleavage effluent. These components may include phenol, cyclohexanone and water, which may be used to provide at least some of the phenol, cyclohexanone or water for mixing with the cleavage feed to attain the desired cleavage reaction mixture composition.

The invention will now be more particularly described with reference to the following non-limiting Example.

EXAMPLE

Three separate tests of the acid catalyzed cleavage of cyclohexylbenzene hydroperoxide were conducted under identical conversion conditions in a stirred tank such as that shown in FIG. 4b. the testing conditions ($t_R/t_M$) and selectivity of byproduct 6-hydroxy-hexanophenone (6-HHP) are provided in the following TABLE I. In TABLE I, "X" is the measured 6-HHP concentration in Test B.

TABLE I

| Test No. | $t_R/t_M$ | 6-HHP selectivity |
|---|---|---|
| A | 2 | 5X |
| B | 20 | X |
| C | 50 | 0.7X |

It is clear from TABLE I above that as the $t_R/t_M$ increased from 2 to 20, the 6-HHP selectivity decreased by 5 times, showing that the undesirable side reaction to produce 6-HHP was reduced significantly. As the $t_R/t_M$ further increased to 50, the 6-HHP selectivity decreased further as a result.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The present application includes but are not limited to the following aspects and/or embodiments:

E1. A process for producing phenol and cyclohexanone, the process comprising:
(a1) supplying reaction components comprising cyclohexylbenzene hydroperoxide and an acid catalyst to a cleavage reaction zone;
(a2) mixing the reaction components under mixing conditions effective to combine the reaction components into a reaction mixture;
(a3) converting at least part of the cyclohexylbenzene hydroperoxide in the reaction mixture under cleavage conditions into phenol and cyclohexanone; and
(b) recovering a cleavage effluent from the cleavage reaction zone, wherein the mixing (a2) is arranged such that the ratio $t_R/t_M$ is at least 10, where $t_R$ is the half-life of cyclohexylbenzene hydroperoxide under the cleavage conditions, and $t_M$ is the time required after injection of a tracer material into the reaction mixture under the mixing conditions for at least 95% by volume of the entire reaction mixture to attain at least 95% of the volume-averaged tracer concentration.

E2. The process of E1, wherein $t_R/t_M$ is at least 50.

E3. The process of E1 or E2, wherein $t_R/t_M$ is at least 100.

E4. The process of any of E1 to E3, wherein the acid catalyst comprises sulfuric acid.

E5. The process of E4, wherein the concentration of sulfuric acid in the reaction mixture is from 50 to 5000 wppm.

E6. The process of any of E1 to E5, further comprising:
(c) recycling part of the cleavage effluent to the cleavage reaction zone as a source of one or more of the reaction components.

E7. The process of any of E1 to E6, wherein the mixing (a2) comprises passing the reaction components through at least one of an in-line static mixer, an in-line orifice plate, an in-line swirl vane assembly and a pump.

E8. The process of any of E1 to E7, wherein the mixing (a2) comprises stirring the reaction components by passing one or more mechanical agitation devices.

E9. The process of any of E1 to E8, wherein the reaction components comprise at least a first stream and a second stream and the mixing (a2) comprises injecting the first stream into the second stream.

E10. The process of any of E1 to E9, wherein the first stream is injected into the second stream using one or more of a T-mixer, a single outlet nozzle, and a multiple outlet nozzle.

E11. The process of any of E1 to E10, wherein the cleavage conditions in the cleavage reaction zone in (a3) include a temperature from 30° C. and to 70° C. and an absolute internal pressure of at least 100 kPa.

E12. A process for producing phenol and cyclohexanone, the process comprising:
(a) hydroalkylating benzene with hydrogen in the presence of a first catalyst under conditions effective to produce a hydroalkylation product comprising cyclohexylbenzene;
(b) contacting at least part of the cyclohexylbenzene from (a) with oxygen in the presence of a second catalyst under oxidation conditions effective to produce an oxidation product comprising cyclohexylbenzene hydroperoxide;
(c1) supplying reaction components comprising cyclohexylbenzene hydroperoxide from (b) and an acid catalyst to a cleavage reaction zone;
(c2) mixing the reaction components under mixing conditions effective to combine the reaction components into a reaction mixture;
(c3) converting at least part of the cyclohexylbenzene hydroperoxide in the reaction mixture under cleavage conditions into phenol and cyclohexanone; and
(d) recovering a cleavage effluent from the cleavage reaction zone, wherein the mixing (c2) is arranged such that the ratio $t_R/t_M$ is at least 10, where $t_R$ is the half-life of cyclohexylbenzene hydroperoxide under the cleavage conditions and $t_M$ is the time required after injection of a tracer material into the reaction mixture under the mixing conditions for at least 95% by volume of the entire reaction mixture to attain at least 95% of the volume-averaged tracer material concentration.

E13. The process of E12, wherein $t_R/t_M$ is at least 50.

E14. The process of E12 or E13, wherein $t_R/t_M$ is at least 100.

E15. The process of any of E12 to E14, wherein the acid catalyst in (c1) comprises sulfuric acid.

E16. The process of E15, wherein the concentration of sulfuric acid in the reaction mixture in (c3) is from 50 to 5000 wppm, based on the total weight of the reaction mixture.

E17. The process of any of E12 to E16, further comprising:
(e) recycling part of the cleavage effluent to the cleavage reaction zone as a source of one or more of the reaction components.

E18. The process of any of E12 to E17, wherein the mixing (c2) comprise passing the reaction components through at least one of an in-line static mixer, an in-line orifice plate, an in-line swirl vane assembly and a pump.

E19. The process of any of E12 to E18, wherein the mixing (c2) comprise stirring the reaction components by using one or more mechanical agitation devices.

E20. The process of any of E12 to E19, wherein the reaction components in (c2) comprise at least a first stream and a second stream and the mixing in (c2) comprises injecting the first stream into the second stream.

E21. The process of any of E12 to E20, wherein the first stream is injected into the second stream using one or more of a T-mixer, a single outlet nozzle, and a multiple outlet nozzle.

E22. The process of any of E12 to E21, wherein the cleavage conditions in (c3) include a temperature in the range from 30° C. and to 70° C. and an absolute internal pressure in the cleavage reaction zone of at least 100 kPa.

E23. The process of any of E12 to E22, wherein the reaction components in (c1) further comprise residual cyclohexylbenzene from the oxidation product.

E24. The process of any of E12 to E23, wherein the reaction mixture in (c3) comprises from 1 wt % to 60 wt % cyclohexylbenzene hydroperoxide, from 1 wt % to 40 wt % cyclohexylbenzene, from 0.1 wt % to 4 wt % water, and from 10 wppm to 1000 wppm sulfuric acid.

E25. The process of E24, wherein the reaction mixture in (c3) further comprises from 20 wt % to 70 wt % phenol and from 20 wt % to 50 wt % cyclohexanone.

The invention claimed is:

1. A process for producing phenol and cyclohexanone, the process comprising:
(a1) supplying reaction components comprising cyclohexylbenzene hydroperoxide and an acid catalyst to a cleavage reaction zone;
(a2) mixing the reaction components under mixing conditions effective to combine the reaction components into a reaction mixture;
(a3) converting at least part of the cyclohexylbenzene hydroperoxide in the reaction mixture under cleavage conditions into phenol and cyclohexanone; and
(b) recovering a cleavage effluent from the cleavage reaction zone,
wherein the mixing (a2) is arranged such that the ratio $t_R/t_M$ is at least 10, where $t_R$ is the half-life of cyclohexylbenzene hydroperoxide under the cleavage conditions, and $t_M$ is the time required after injection of a tracer material into the reaction mixture under the mixing conditions for at least 95% by volume of the entire reaction mixture to attain at least 95% of the volume-averaged tracer concentration.

2. The process of claim 1, wherein $t_R/t_M$ is at least 50.

3. The process of claim 1, wherein the acid catalyst comprises sulfuric acid.

4. The process of claim 3, wherein the concentration of sulfuric acid in the reaction mixture is from 50 to 5000 wppm.

5. The process of claim 1, further comprising:
(d) recycling part of the cleavage effluent to the cleavage reaction zone as a source of one or more of the reaction components.

6. The process of claim 1, wherein the mixing (a2) comprises passing the reaction components through at least one of an in-line static mixer, an in-line orifice plate, an in-line swirl vane assembly and a pump.

7. The process of claim 1, wherein the mixing (a2) comprises stirring the reaction components through one or more mechanical agitation devices.

8. The process of claim 1, wherein the reaction components comprise at least a first stream and a second stream and the mixing (a2) comprises injecting the first stream into the second stream.

9. The process of claim 8, wherein the first stream is injected into the second stream using one or more of a T-mixer, a single outlet nozzle, and a multiple outlet nozzle.

10. The process of claim 1, wherein the cleavage conditions in (a3) include a temperature in the range from 30° C. and to 70° C. and an absolute internal pressure of at least 100 kPa.

11. The process of claim 1, further comprising:
(e) hydroalkylating benzene with hydrogen in the presence of a first catalyst, desirably a metal-containing zeolite of the MCM-22 family, under conditions effective to produce a hydroalkylation product comprising cyclohexylbenzene;
(f) contacting at least part of the cyclohexylbenzene from (e) with oxygen in the presence of a second catalyst, desirably a cyclic imide, under oxidation conditions effective to produce an oxidation product comprising cyclohexylbenzene hydroperoxide; and
(g) supplying at least part of the cyclohexylbenzene hydroperoxide from (e) to the cleavage reaction zone in (a1).

12. The process of claim 11, wherein the reaction components further comprise residual cyclohexylbenzene from the oxidation product.

13. The process of claim 1, wherein the reaction mixture comprises from 1 wt % to 60 wt % cyclohexylbenzene hydroperoxide, from 1 wt % to 40 wt % cyclohexylbenzene, from 0.1 wt % to 4 wt % water, and from 10 wppm to 1000 wppm sulfuric acid.

14. The process of claim 13, wherein the reaction mixture further comprises from 20 wt % to 70 wt % phenol and from 20 wt % to 50 wt % cyclohexanone.

* * * * *